(12) United States Patent
Akiyama et al.

(10) Patent No.: US 7,491,802 B2
(45) Date of Patent: Feb. 17, 2009

(54) ANTI-BAMBI ANTIBODY AND DIAGNOSTIC OR REMEDY FOR COLON CANCER AND LIVER CANCER

(75) Inventors: Tetsu Akiyama, Tokyo (JP); Takashi Sekiya, Tokyo (JP); Susumu Ohwada, Gunma (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/558,567

(22) PCT Filed: May 27, 2004

(86) PCT No.: PCT/JP2004/007677

§ 371 (c)(1),
(2), (4) Date: Mar. 28, 2006

(87) PCT Pub. No.: WO2004/106515

PCT Pub. Date: Dec. 9, 2004

(65) Prior Publication Data

US 2007/0065446 A1    Mar. 22, 2007

(30) Foreign Application Priority Data

May 28, 2003    (JP) ............................. 2003-151302

(51) Int. Cl.
*C07K 16/00* (2006.01)
(52) U.S. Cl. ............................... 530/388.1; 530/388.23
(58) Field of Classification Search ........................ None
See application file for complete search history.

(56) References Cited

U.S. PATENT DOCUMENTS

| 5,747,273 A * | 5/1998 | Khosravi et al. ........... 435/7.94 |
| 5,997,865 A * | 12/1999 | Bennett et al. ............ 424/130.1 |
| 6,001,621 A * | 12/1999 | Godowski et al. ........... 435/194 |
| 6,180,370 B1 * | 1/2001 | Queen et al. ............... 435/69.6 |

FOREIGN PATENT DOCUMENTS

| WO | WO 99/32619 A1 | 7/1999 |
| WO | WO 02/059377 A2 | 8/2002 |
| WO | WO 03/055443 A2 | 7/2003 |

OTHER PUBLICATIONS

Degen et al. Expression of nma, a novel gene, inversely correlates with the metastatic potential of human melanoma cell lines and xenografts. Int J Cancer. Feb. 8, 1996;65(4):460-5.*
Burgess WH, Shaheen AM, Ravera M, Jaye M, Donohue PJ, Winkles JA. Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.*
Lin MC, Wright DE, Hruby VJ, Rodbell M. Structure-function relationships in glucagon: properties of highly purified des-His-1-, monoiodo-, and (des-Asn-28, Thr-29)(homoserine lactone-27)-glucagon. Biochemistry. Apr. 22, 1975;14(8):1559-63.*
Campbell M. Monoclonal antibody technology. Chapter 1. Elsevier Science Publishers B.V., 1984.*
Lazar E, Watanabe S, Dalton S, Sporn MB. Transforming growth factor alpha: mutation of aspartic acid 47 and leucine 48 results in different biological activities. Mol Cell Biol. Mar. 1988;8(3):1247-52.*
Schwartz GP, Burke GT, Katsoyannis PG. A superactive insulin: [B10-aspartic acid]insulin(human). Proc Natl Acad Sci U S A. Sep. 1987;84(18):6408-11.*
Degen W. G. et al., "Expression of nma, a novel gene, inversely correlates with the metastatic potential of Human melanoma cell lines and Xenografts", Int. J. Cancer, 1996, vol. 165, No. 4, pp. 460 to 465.
D. Onichtchouk et al., "Silencing of TGF-β signalling by the pseudoreceptor BAMBI", Nature, 1999, vol. 401, pp. 480 to 485.
M. J. Calonge et al., "Smad4/DPC4 Silencing and Hyperactive Ras Jointly Disrupt Transforming Growth Factor-β Antiproliferative Responses in Colon Cancer Cells", J. Biol. Chem., 1999, vol. 274, No. 47, pp. 33637 to 33643.
K. Miyazono, "Signal transduction and carcinogenesis: Mechanism of TGF-β signalling", Molecular Medicine (Tokyo), 1998, vol. 35, No. 6, pp. 746 to 752.
T. Sekiya et al., "Identification of BMP and Activin Membrane-Bound Inhibitor (BAMBI), and Inhibitor of Transfoming Growth Factor-β Signaling, as a target of the β-Catenin Pathway in Colorectal Tumor Cells". J. Biol. Chem., Feb. 2004, vol. 279, No. 8, pp. 6840 to 6846.
Wieser R: "The Transforming Growth Factor Beta Signaling Pathway In Tumorigenesis" Current Opinion In Oncology, Current Science LTD, US, vol. 13, No. 1, Jan. 2001, pp. 70-77.
O'Dwyer Peter J. et al.: "Epidermal growth factor receptor-targeted therapy in colorectal cancer." Seminars In Oncology. Oct. 2002, vol. 29, No. 5 Suppl 14, Oct. 2002, pp. 10-17.
Baldus S. E.: "[Clinical, pathological and molecular prognostic factors in colorectal carcinomas]" Der Pathologe. Feb. 2003, vol. 24, No. 1, Feb. 2003, pp. 49-60.
Sasaki Takamitsu et al.: "Effect of Nma on growth inhibition by TGF-beta in human gastric carcinoma cell lines." Oncology Reports. Jun. 2004, vol. 11, No. 6, Jun. 2004, pp. 1219-1223.
Smirnov et al., "Global Gene Expression Profiling of Circulating Tumor Cells" Cancer Research (2005) 65:4993-4997.

* cited by examiner

*Primary Examiner*—Larry R. Helms
*Assistant Examiner*—Meera Natarajan
(74) *Attorney, Agent, or Firm*—Jones Day

(57) ABSTRACT

The present invention provides an antibody (anti-BAMBI antibody) which recognizes a polypeptide having the amino acid sequence of SEQ ID No: 1 or a polypeptide having an amino acid sequence containing deletion, substitution or addition of one or more amino acids as compared to the amino acid sequence of SEQ ID No: 1, a method for manufacturing same, a therapeutic agent for colon cancer or liver cancer comprising an anti-BAMBI antibody, a diagnostic agent comprising a primer or probe for detecting the BAMBI gene, and a therapeutic agent for colon cancer or liver cancer comprising a vector which generates BAMBI dsRNA, and the like.

11 Claims, 7 Drawing Sheets

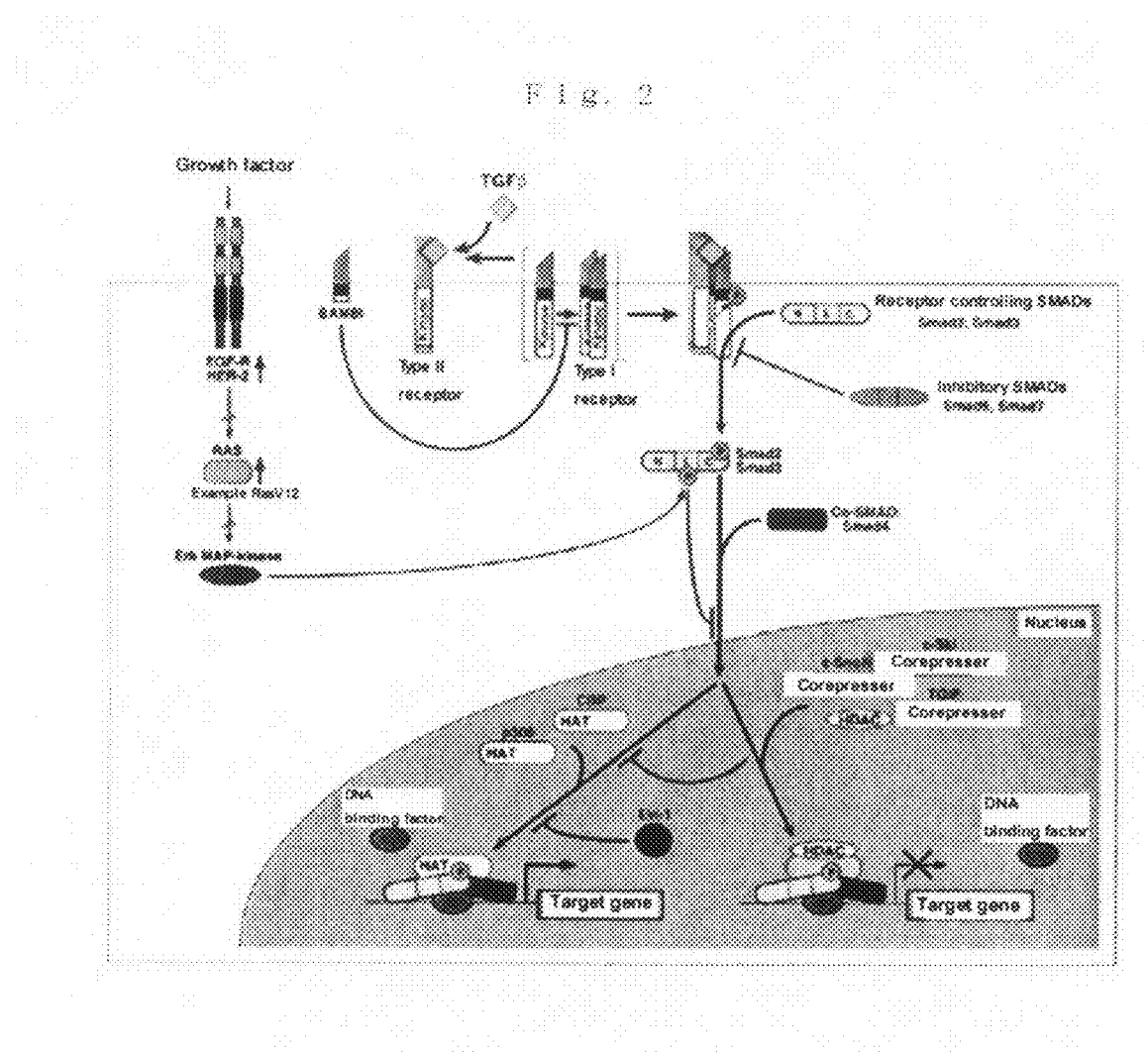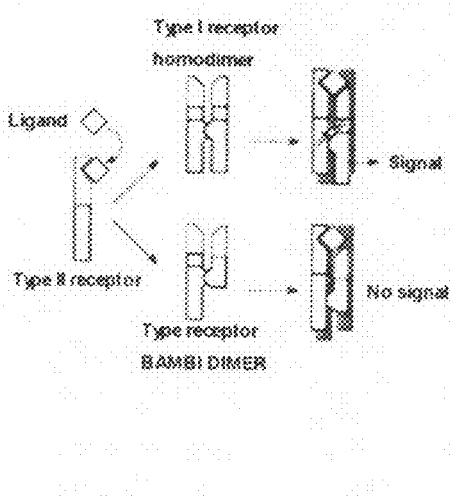
Fig. 2

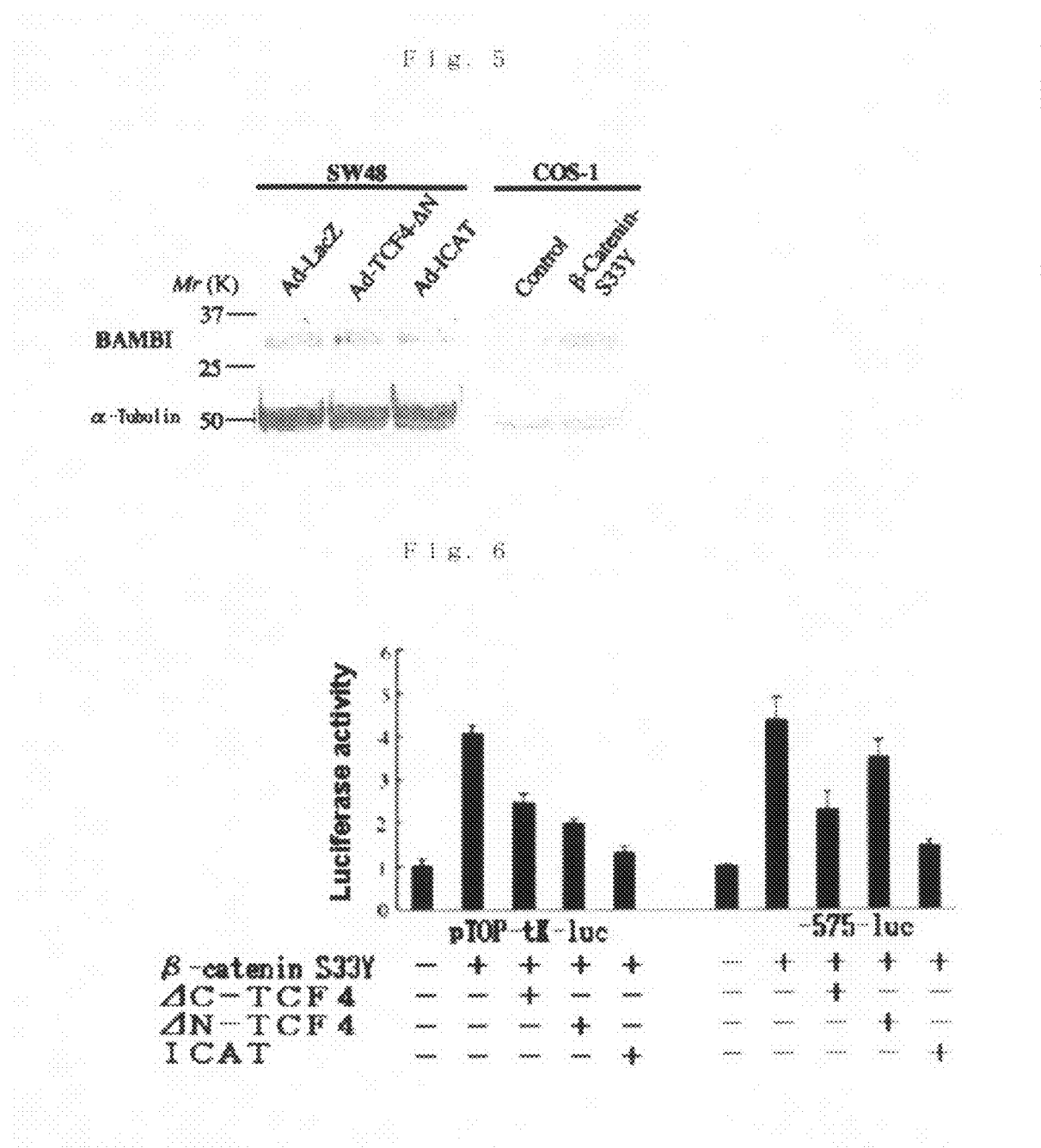

SEQUENCE LISTING

<160> NUMBER OF SEQ ID NOS: 35

<210> SEQ ID NO 1
<211> LENGTH: 260
<212> TYPE: PRT

<213> ORGANISM: Homo sapiens

<400> SEQUENCE: 1

| | | | | | | | | | | | | | | |
|---|---|---|---|---|---|---|---|---|---|---|---|---|---|---|
| Met | Asp | Arg | His | Ser | Ser | Tyr | Ile | Phe | Ile | Trp | Leu | Gln | Leu | Glu | Leu |
| 1 | | | | 5 | | | | | 10 | | | | | 15 | |
| Cys | Ala | Met | Ala | Val | Leu | Leu | Thr | Lys | Gly | Glu | Ile | Arg | Cys | Tyr | Cys |
| | | | 20 | | | | | 25 | | | | | 30 | | |
| Asp | Ala | Ala | His | Cys | Val | Ala | Thr | Gly | Tyr | Met | Cys | Lys | Ser | Glu | Leu |
| | | 35 | | | | | 40 | | | | | 45 | | | |
| Ser | Ala | Cys | Phe | Ser | Arg | Leu | Leu | Asp | Pro | Gln | Asn | Ser | Asn | Ser | Pro |
| | 50 | | | | | 55 | | | | | 60 | | | | |
| Leu | Thr | His | Gly | Cys | Leu | Asp | Ser | Leu | Ala | Ser | Thr | Thr | Asp | Ile | Cys |
| 65 | | | | 70 | | | | | 75 | | | | | 80 | |
| Gln | Ala | Lys | Gln | Ala | Arg | Asn | His | Ser | Gly | Thr | Thr | Ile | Pro | Thr | Leu |
| | | | | 85 | | | | | 90 | | | | | 95 | |
| Glu | Cys | Cys | His | Glu | Asp | Met | Cys | Asn | Tyr | Arg | Gly | Leu | His | Asp | Val |
| | | | 100 | | | | | 105 | | | | | 110 | | |
| Leu | Ser | Pro | Pro | Arg | Gly | Glu | Ala | Ser | Gly | Gln | Gly | Asn | Arg | Tyr | Gln |
| | | 115 | | | | | 120 | | | | | 125 | | | |
| His | Asp | Gly | Ser | Arg | Asn | Leu | Ile | Thr | Lys | Val | Gln | Glu | Leu | Thr | Ser |
| | 130 | | | | | 135 | | | | | 140 | | | | |
| Ser | Lys | Glu | Leu | Trp | Phe | Arg | Ala | Ala | Val | Ile | Ala | Val | Pro | Ile | Ala |
| 145 | | | | | 150 | | | | | 155 | | | | | 160 |
| Gly | Gly | Leu | Ile | Leu | Val | Leu | Leu | Ile | Met | Leu | Ala | Leu | Arg | Met | Leu |
| | | | 165 | | | | | 170 | | | | | 175 | | |
| Arg | Ser | Glu | Asn | Lys | Arg | Leu | Gln | Asp | Gln | Arg | Gln | Gln | Met | Leu | Ser |
| | | | 180 | | | | | 185 | | | | | 190 | | |
| Arg | Leu | His | Tyr | Ser | Phe | His | Gly | His | His | Ser | Lys | Lys | Gly | Gln | Val |
| | | 195 | | | | | 200 | | | | | 205 | | | |
| Ala | Lys | Leu | Asp | Leu | Glu | Cys | Met | Val | Pro | Val | Ser | Gly | His | Glu | Asn |
| | 210 | | | | | 215 | | | | | 220 | | | | |
| Cys | Cys | Leu | Thr | Cys | Asp | Lys | Met | Arg | Gln | Ala | Asp | Leu | Ser | Asn | Asp |
| 225 | | | | | 230 | | | | | 235 | | | | | 240 |
| Lys | Ile | Leu | Ser | Leu | Val | His | Trp | Gly | Met | Tyr | Ser | Gly | His | Gly | Lys |
| | | | 245 | | | | | 250 | | | | | 255 | | |
| Leu | Glu | Phe | Val | | | | | | | | | | | | |
| | | | 260 | | | | | | | | | | | | |

<210> SEQ ID NO 2
<211> LENGTH: 1521
<212> TYPE: DNA
<213> ORGANISM: Homo sapiens

<400> SEQUENCE: 2

```
ctggcgcggg cgggagctgc ggcggatacc cttgcgtgct gtggagaccc tactctcttc      60
gctgagaacg gccgctagcg gggactgaag gccgggagcc cactcccgac ccggggctag     120
cgtgcgtccc tagagtcgag cggggcaagg gagccagtgg ccgccgacgg ggaccgggga    180
aacttttctg ggctcctgga gagccctgta gccgcgctcc atgctccggc agcggcccga    240
aacccagccc cgccgctgac ggagcccgcc gctccgggca gggcccatgc cctgcgcgct    300
ccgggggtcg tagctgccgc cgagccgggg ctccggaagc cggcggggc gccgcggccg    360 tgcggggcgt caatggatcg ccactccagc tacatcttca tctggctgca gctggagctc    420
tgcgccatgg ccgtgctgct caccaaaggt gaaattcgat gctactgtga tgctgcccac    480
```

```
tgtgtagcca ctggttatat gtgtaaatct gagctcagcg cctgcttctc tagacttctt    540
gatcctcaga actcaaattc cccactcacc catggctgcc tggactctct tgcaagcacg    600
acagacatct gccaagccaa acaggcccga accactctg gcaccaccat acccacattg     660
gaatgctgtc atgaagacat gtgcaattac agagggctgc acgatgttct ctctcctccc    720
aggggtgagg cctcaggaca aggaaacagg tatcagcatg atggtagcag aaaccttatc    780
accaaggtgc aggagctgac ttcttccaaa gagttgtggt tccgggcagc ggtcattgcc    840
gtgcccattg ctggagggct gattttagtg ttgcttatta tgttggccct gaggatgctt    900
cgaagtgaaa ataagaggct gcaggatcag cggcaacaga tgctctcccg tttgcactac    960
agctttcacg acaccattc caaaaggggg caggttgcaa agttagactt ggaatgcatg    1020
gtgccggtca gtgggcacga gaactgctgt ctgacctgtg ataaaatgag acaagcagac   1080
ctcagcaacg ataagatcct ctcgcttgtt cactgggca tgtacagtgg gcacgggaag    1140
ctggaattcg tatgacggag tcttatctga actacactta ctgaacagct tgaaggcctt   1200
ttgagttctg ctggacagga gcactttatc tgaagacaaa ctcatttaat catctttgag   1260
agacaaaatg acctctgcaa acagaatctt ggatatttct tctgaaggat tatttgcaca   1320
gacttaaata cagttaaatg tgttatttgc ttttaaaatt ataaaaagca aagagaagac   1380
tttgtacaca ctgtcaccag ggttatttgc atccaaggga gctggaattg agtacctaaa   1440
taaacaaaaa tgtgccctat gtaagcttct acatcttgat ttattgtaaa gatttaaaag   1500
aaatatatat attttgtctg a                                             1521
```

<210> SEQ ID NO 3
<211> LENGTH: 19
<212> TYPE: DNA
<213> ORGANISM: Artificial Sequence
<220> FEATURE:
<223> OTHER INFORMATION: synthetic DNA

<400> SEQUENCE: 3
ccactctggc accaccata                                                  19

<210> SEQ ID NO 4
<211> LENGTH: 19
<212> TYPE: DNA
<213> ORGANISM: Artificial Sequence
<220> FEATURE:
<223> OTHER INFORMATION: synthetic DNA

<400> SEQUENCE: 4
cagatgctct cccgtttgc                                                  19

<210> SEQ ID NO 5
<211> LENGTH: 19
<212> TYPE: DNA
<213> ORGANISM: Artificial Sequence
<220> FEATURE:
<223> OTHER INFORMATION: synthetic DNA

<400> SEQUENCE: 5
ctgctgtctg acctgtgat                                                  19

<210> SEQ ID NO 6
<211> LENGTH: 25
<212> TYPE: DNA
<213> ORGANISM: Artificial Sequence
<220> FEATURE:
<223> OTHER INFORMATION: synthetic DNA

```
<400> SEQUENCE: 6
gctgcagagg attgattagc ggtag                                              25

<210> SEQ ID NO 7
<211> LENGTH: 25
<212> TYPE: DNA
<213> ORGANISM: Artificial Sequence
<220> FEATURE:
<223> OTHER INFORMATION: synthetic DNA

<400> SEQUENCE: 7
ctaccgctaa tcaatcctct gcagc                                              25

<210> SEQ ID NO 8
<211> LENGTH: 27
<212> TYPE: DNA
<213> ORGANISM: Artificial Sequence
<220> FEATURE:
<223> OTHER INFORMATION: synthetic DNA

<400> SEQUENCE: 8
ctctgtgtct agttaaatgt atctctg                                            27

<210> SEQ ID NO 9
<211> LENGTH: 27
<212> TYPE: DNA
<213> ORGANISM: Artificial Sequence
<220> FEATURE:
<223> OTHER INFORMATION: synthetic DNA

<400> SEQUENCE: 9
cagagataca tttaactaga cacagag                                            27

<210> SEQ ID NO 10
<211> LENGTH: 27
<212> TYPE: DNA
<213> ORGANISM: Artificial Sequence
<220> FEATURE:
<223> OTHER INFORMATION: synthetic DNA

<400> SEQUENCE: 10
ctctaagtgt agttatatct ctgaatg                                            27

<210> SEQ ID NO 11
<211> LENGTH: 27
<212> TYPE: DNA
<213> ORGANISM: Artificial Sequence
<220> FEATURE:
<223> OTHER INFORMATION: synthetic DNA

<400> SEQUENCE: 11
cattcagaga tataactaca cttagag                                            27

<210> SEQ ID NO 12
<211> LENGTH: 26
<212> TYPE: DNA
<213> ORGANISM: Artificial Sequence
<220> FEATURE:
<223> OTHER INFORMATION: synthetic DNA

<400> SEQUENCE: 12
ctggaaatat agaaagcggg cagaac                                             26

<210> SEQ ID NO 13
```

```
<211> LENGTH: 26
<212> TYPE: DNA
<213> ORGANISM: Artificial Sequence
<220> FEATURE:
<223> OTHER INFORMATION: synthetic DNA

<400> SEQUENCE: 13
gttctgcccg ctttctatat ttccag                                          26

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 14
ctaaaagttc atgcagttaa atttggg                                         27

<210> SEQ ID NO 15
<211> LENGTH: 27
<212> TYPE: DNA
<213> ORGANISM: Artificial Sequence
<220> FEATURE:
<223> OTHER INFORMATION: synthetic DNA

<400> SEQUENCE: 15
cccaaattta actgcatgaa cttttag                                         27

<210> SEQ ID NO 16
<211> LENGTH: 37
<212> TYPE: DNA
<213> ORGANISM: Artificial Sequence
<220> FEATURE:
<223> OTHER INFORMATION: synthetic DNA

<400> SEQUENCE: 16
catgaattcc gccaccatgg atcgccactc cagctac                              37

<210> SEQ ID NO 17
<211> LENGTH: 31
<212> TYPE: DNA
<213> ORGANISM: Artificial Sequence
<220> FEATURE:
<223> OTHER INFORMATION: synthetic DNA

<400> SEQUENCE: 17
catctcgagt acgaacacca gcaacccgtg c                                    31

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 18
catgaattcg cttccgtgtc caggttccct cc                                   32

<210> SEQ ID NO 19
<211> LENGTH: 33
<212> TYPE: DNA
<213> ORGANISM: Artificial Sequence
<220> FEATURE:
<223> OTHER INFORMATION: synthetic DNA
```

<400> SEQUENCE: 19
catctcgagc tagcctagca ggttcgggga ggg                     33

<210> SEQ ID NO 20
<211> LENGTH: 25
<212> TYPE: DNA
<213> ORGANISM: Artificial Sequence
<220> FEATURE:
<223> OTHER INFORMATION: synthetic DNA

<400> SEQUENCE: 20
gctgcagagg ctttgttagc ggtag                              25

<210> SEQ ID NO 21
<211> LENGTH: 25
<212> TYPE: DNA
<213> ORGANISM: Artificial Sequence
<220> FEATURE:
<223> OTHER INFORMATION: synthetic DNA

<400> SEQUENCE: 21
ctaccgctaa caaagcctct gcagc                              25

<210> SEQ ID NO 22
<211> LENGTH: 27
<212> TYPE: DNA
<213> ORGANISM: Artificial Sequence
<220> FEATURE:
<223> OTHER INFORMATION: synthetic DNA

<400> SEQUENCE: 22
ctctgtgtct ctttgaatgt atctctg                            27

<210> SEQ ID NO 23
<211> LENGTH: 27
<212> TYPE: DNA
<213> ORGANISM: Artificial Sequence
<220> FEATURE:
<223> OTHER INFORMATION: synthetic DNA

<400> SEQUENCE: 23
cagagataca ttcaaagaga cacagag                            27

<210> SEQ ID NO 24
<211> LENGTH: 27
<212> TYPE: DNA
<213> ORGANISM: Artificial Sequence
<220> FEATURE:
<223> OTHER INFORMATION: synthetic DNA

<400> SEQUENCE: 24
ctctaagtgt ctttgtatct ctgaatg                            27

<210> SEQ ID NO 25
<211> LENGTH: 27
<212> TYPE: DNA
<213> ORGANISM: Artificial Sequence
<220> FEATURE:
<223> OTHER INFORMATION: synthetic DNA

<400> SEQUENCE: 25
cattcagaga tacaaagaca cttagag                            27

<210> SEQ ID NO 26

```
<211> LENGTH: 26
<212> TYPE: DNA
<213> ORGANISM: Artificial Sequence
<220> FEATURE:
<223> OTHER INFORMATION: synthetic DNA

<400> SEQUENCE: 26
ctggaaatat caaaggcggg cagaac                                              26

<210> SEQ ID NO 27
<211> LENGTH: 26
<212> TYPE: DNA
<213> ORGANISM: Artificial Sequence
<220> FEATURE:
<223> OTHER INFORMATION: synthetic DNA

<400> SEQUENCE: 27
gttctgcccg cctttgatat ttccag                                              26

<210> SEQ ID NO 28
<211> LENGTH: 27
<212> TYPE: DNA
<213> ORGANISM: Artificial Sequence
<220> FEATURE:
<223> OTHER INFORMATION: synthetic DNA

<400> SEQUENCE: 28
ctaaaagttc atgcctttga atttggg                                             27

<210> SEQ ID NO 29
<211> LENGTH: 27
<212> TYPE: DNA
<213> ORGANISM: Artificial Sequence
<220> FEATURE:
<223> OTHER INFORMATION: synthetic DNA

<400> SEQUENCE: 29
cccaaattca aaggcatgaa cttttag                                             27

<210> SEQ ID NO 30
<211> LENGTH: 20
<212> TYPE: DNA
<213> ORGANISM: Artificial Sequence
<220> FEATURE:
<223> OTHER INFORMATION: synthetic DNA

<400> SEQUENCE: 30 cagggtgag gcctcaggac                                                      20

<210> SEQ ID NO 31
<211> LENGTH: 23
<212> TYPE: DNA
<213> ORGANISM: Artificial Sequence
<220> FEATURE:
<223> OTHER INFORMATION: synthetic DNA

<400> SEQUENCE: 31
caaattccag ctcccttgga tgc                                                 23

<210> SEQ ID NO 32
<211> LENGTH: 20
<212> TYPE: DNA
<213> ORGANISM: Artificial Sequence
<220> FEATURE:
<223> OTHER INFORMATION: synthetic DNA

<400> SEQUENCE: 32
```

```
gccagccggc accatctgtg                                               20

<210> SEQ ID NO 33
<211> LENGTH: 20
<212> TYPE: DNA
<213> ORGANISM: Artificial Sequence
<220> FEATURE:
<223> OTHER INFORMATION: synthetic DNA

<400> SEQUENCE: 33
cgaagcccac tggccgattc                                               20

<210> SEQ ID NO 34
<211> LENGTH: 20
<212> TYPE: DNA
<213> ORGANISM: Artificial Sequence
<220> FEATURE:
<223> OTHER INFORMATION: synthetic DNA

<400> SEQUENCE: 34
acactgtgcc catctacgag                                               20

<210> SEQ ID NO 35
<211> LENGTH: 20
<212> TYPE: DNA
<213> ORGANISM: Artificial Sequence
<220> FEATURE:
<223> OTHER INFORMATION: synthetic DNA

<400> SEQUENCE: 35 agtcctgcttgctgatccac                                                20
```

ANTI-BAMBI ANTIBODY AND DIAGNOSTIC OR REMEDY FOR COLON CANCER AND LIVER CANCER

This application is the United States National Stage of International Application No. PCT/JP2004/007677, filed May 27, 2004, which is incorporated by reference herein in its entirety.

BACKGROUND OF THE INVENTION

1. Field of the Invention

The present invention relates to an antibody to the BAMBI protein, to a manufacturing method for the antibody, and to a diagnostic agent or therapeutic agent for colon cancer and liver cancer containing the antibody.

2. Description of the Related Art

CEA, CA19-9 and other tumor markers are considered to be effective in the diagnosis of colon cancer. For example, Japanese Patent Application Laid-open No. 2000-323499 discloses a tumor marker assay method for detecting tumor markers in blood components. However, these tumor markers are not very reliable because they do not always occur in association with cancer, and abnormal values may be due to causes other than cancer.

It has also been shown that APC, RAS, p53 and other genes are associated with the development of colon cancer. However, no genetic diagnosis method that specifically detects colon cancer has yet been established for practical use.

In the area of chemotherapy for the treatment of colon cancer, alkylating agents, antimetabolites and the like have been studied which are cytotoxic to cancer cells by blocking cancer gene transcription, cleaving DNA or the like, but these drugs have side-effects because they do not act selectively only on cancer cells but also affect normal cells.

Colon cancers are one of the most common kinds of tumors, and in recent years the number of patients has increased in Japan and is expected to increase still further. Therefore, it is an object of the present invention to provide a diagnostic agent and therapeutic agent capable of reliably diagnosing and treating colon cancer.

SUMMARY OF THE INVENTION

The mechanism of colon cancer onset has been studied in detail at the molecular level, and it is known that abnormalities in the Wnt signaling system and the K-ras, p53, TGF-beta and other signaling systems occur with high frequency. In particular, abnormalities of the Wnt signaling system occur at the earliest stage of colon cancer, and are thought to hold the key to colon cancer development, so the inventors attempted to develop a novel diagnostic agent and therapeutic agent for colon cancer by studying the Wnt signaling system in colon cancer.

Wnt signaling is an intercellular signaling system that has a variety of functions in forming the body, ranging from, for example, initial body axis formation and cell movement accompanying gastrocoele invagination during embryogenesis to subsequent organ formation. It also plays an important role in controlling cell proliferation and differentiation in adults, and it is known that constant activation of the Wnt signaling pathway due to a breakdown in its control mechanism is an important factor in cancer cell development. When the Wnt signaling pathway is activated, beta-catenin accumulates in the cell, and when this beta-catenin interacts with transcription factors in the TCF/LEF family it activates expression of target genes such as cyclin D and c-myc that play an important role in cell proliferation. Beta-catenin accumulation is seen in a variety of tumor cells. When there is no Wnt signal, beta-catenin interacts with axin, GSK-3β and tumor suppressor APC and is phosphorylated by the action of beta-catenin or GSK-3β and broken down in the cell. FIG. 1 shows an outline of the Wnt signaling system.

However, in colon cancer abnormalities occur in constituent factors APC, beta-catenin and axin of the Wnt signaling pathway, reducing the breakdown of beta-catenin. Moreover, axin abnormalities have also been discovered in liver cancer, and beta-catenin abnormalities in skin cancer, liver cancer, ovarian cancer and the like. It is thought that the accumulated beta-catenin causes canceration of cells by forming a complex with TCF/LEF transcription factors and abnormally activating transcription of target genes. Consequently, discovering a target gene for the beta-catenin/TCF complex is extremely important as a means of clarifying the mechanism of tumorigenesis.

Therefore, the inventors searched for novel factors that negatively control the Wnt signaling pathway by blocking the formation of complexes with TCF/LEF through binding to beta-catenin, and discovered the ICAT gene (Tago et al, *Gene and Development* Vol. 14, p. 1741-1749).

Since aberrant activation of Wnt signaling is a critical factor in tumor development, ICAT, which represses Wnt signaling, would seem to hold promise for controlling the onset of tumors. In fact, when the inventors used an adenovirus to cause expression of ICAT in cancer cells and studied the growth-suppressing effects, they discovered that ICAT specifically inhibits the growth of colon cancer and liver cancer with abnormal Wnt signaling (APC, beta-catenin and axin abnormalities). On the other hand, ICAT does not exhibit a growth-suppressing effect on normal cells or cancer cells which have developed by another mechanism (*Cancer Research* Vol. 62, 3322-3326). That is, ICAT is thought to suppress growth of colon cancer cells by suppressing transcription activation that has been increased by abnormalities in the Wnt signaling pathway.

The interactions of the Wnt signaling system are shown in the Table 1 below.

TABLE 1

| Wnt signaling-related genes | | |
|---|---|---|
| Effect on signaling | Substance | Effect mechanism |
| Suppression | APC, axin, GSK-3β | Forms complex with β-catenin, inducing breakdown of β-catenin |
| | ICAT | Blocks binding of β-catenin and TCF |
| Promotion | β-catenin, TCF | β-catenin binds with transcription factors Tcf/Lef and exhibits transcription activity |

In these specifications, APC is the Adenomatosis Polyposis Coli gene, Dsh is Dishevelled, GSK-3β is glycogen synthase kinase-3β, TCF is T cell-specific transcription factor, and Fz is Frizzled homolog.

Moreover, based on an assumption that a gene transcription of which is activated by Wnt signaling, which is important for cancer cell growth, could be a target gene for suppressing growth of cancer cells, the inventors attempted to identify a gene transcription of which is suppressed by the effect on colon cancer cells of ICAT, which negatively controls Wnt signaling. When a cDNA subtraction DNA chip was used to search for genes expression of which is reduced by the effect of ICAT in colon cancer cell line SW48 cells in which the Wnt signaling pathway is constantly activated, the BAMBI gene was isolated.

BAMBI (BMP and activin membrane bound inhibitor, BMP: bone morphogenetic protein) is a transmembrane protein with an estimated 260 amino acids (see SEQ ID No: 1 for hBAMBI) which was originally isolated from *Xenopus*, and its extracellular domain is extremely similar to the extracellular domain of TGF-beta receptor I, but unlike TGF-beta receptor I, BAMBI has no serine/threonine kinase domain in the intracellular region. In *Xenopus* embryos, BAMBI expression follows BMP4 expression, so it is thought that BAMBI expression is controlled by BMP4 (*Nature* 401, 480-485). Human BAMBI was cloned in 1996 (called "NMA": *Int. J. Cancer* 65, 460-465, 1996).

BAMBI forms a heterodimer with TGF-beta receptor I and also interacts with TGF-beta receptor II, and since in normal cells TGF-beta receptor I and TGF-beta receptor II form a complex, it is thought that BAMBI blocks the TGF-beta signaling system by interfering with the formation of this complex (see FIG. 2).

TGF-beta is a cytokine with unique biological activity that is involved in suppressing the growth of many epithelial cells. When TGF-beta binds with TGF-beta receptor II it promotes serine/threonine kinase activity within the TGF-beta receptor II molecule, and TGF-beta receptor I is phosphorylated by this kinase. The phosphorylated TGF-beta receptor I binds with Smad2 and Smad3, and the serine/threonine kinase within the TGF-beta receptor I molecule, which has been activated by phosphorylation, in turn phosphorylates the Smad2 and Smad3. The phosphorylated Smad2 and Smad3 form complexes with Smad4 and migrate inside the nucleus, where they induce activation of target gene transcription. Abnormalities of TGF-beta receptor II, Smad2 and/or Smad4 are found in many colon cancer cells, and it is known that growth suppression by TGF-beta does not operate in these cells.

The relationship between TGF-beta signaling and Smad is summarized in Table 2.

TABLE 2

Comparison of 3 types of Smad

| Name | Characteristics |
| --- | --- |
| R-Smad (receptor-regulated Smad) | Transmits characteristic signal through TGF-beta and BMP pathways |
| Co-Smad (common-mediator Smad) | Involved in all pathways, forms complex with R-Smad |
| I-Smad (Inhibitory-Smad) | Acts to inhibit R-Smad and Co-Smad |

Therefore, after discovering that colon cancer and liver cancer could be detected and diagnosed by preparing antibodies to BAMBI and BAMBI primers or probes, the inventors also discovered that colon cancer and liver cancer could be treated using antibodies to BAMBI and siRNA prepared based on a gene encoding BAMBI, and completed the present invention.

That is, the present invention provides the following antibody, method for preparing the antibody, diagnostic agent for colon cancer and liver cancer, and therapeutic agent for colon cancer or liver cancer.

1. An antibody which recognizes a polypeptide having the amino acid sequence of SEQ ID No: 1 or a polypeptide having an amino acid sequence containing deletion, substitution or addition of one or more amino acids as compared to the amino acid sequence of SEQ ID No: 1.

2. The antibody according to (1) above, which specifically recognizes the polypeptide of SEQ ID No: 1.

3. The antibody according to (1) above, which recognizes a polypeptide having 50 or more contiguous amino acid residues in the amino acid sequence of SEQ ID No: 1.

4. The antibody according to (3) above, which recognizes a polypeptide having the amino acid residues of the regions of amino acids 45 through 147 and/or 177 through 241 in the amino acid sequence of SEQ ID No: 1.

5. The antibody according to (1) above, which is a monoclonal antibody.

6. A method for manufacturing an antibody comprising the steps of culturing transformed cells that produce the antibody according to (1) above, and collecting the antibody produced by the cells.

7. A diagnostic agent for colon cancer or liver cancer comprising an antibody according to any of (1) through (6) above.

8. A therapeutic agent for colon cancer or liver cancer comprising an antibody according to any of (1) through (6) above.

9. A diagnostic agent for colon cancer or liver cancer comprising a primer comprising any 15 or more nucleotides of a gene having the nucleotide sequence of SEQ ID No: 2.

10. A diagnostic agent for colon cancer or liver cancer comprising a probe that includes a gene fragment having the nucleotide sequence of SEQ ID No: 2.

11. A therapeutic agent for colon cancer or liver cancer comprising a double-stranded RNA which corresponds to 15 to 30 contiguous nucleotides of a gene having the nucleotide sequence of SEQ ID No: 2, and which generates RNA interference.

12. The therapeutic agent for colon cancer or liver according to (11) above, wherein the sequence of 15 to 30 contiguous nucleotides is CCACTCTGGCACCACCATA (SEQ ID No: 3), CAGATGCTCTCCCGTTTGC (SEQ ID No: 4) or CTGCTGTCTGACCTGTGAT (SEQ ID No: 5).

BRIEF DESCRIPTION OF THE SEVERAL VIEWS OF THE DRAWINGS

FIG. 2 is an outline showing the interactions between BAMBI and TGFβ receptor I and TGFβ receptor II.

FIG. 5 shows the results of an investigation of changes in BAMBI expression due to transcriptional activation via beta-catenin-TCF. The left side shows the results when adenoviruses were used to cause expression of ICAT and TCF-4 dominant negative mutants in SW48 cells, and the cell extracts were immunoblotted using anti-BAMBI N-terminal antibodies and anti-alpha-Tublin antibodies. Total RNA was also extracted and Northern blotted using BAMBI- and G3PDH-specific probes. The right side shows the results when an adenovirus was used to cause expression of beta-catenin-S33Y in COS-1 cells, and a cell extract was prepared and immunoblotted using anti-BAMBI N-terminal antibodies or anti-alpha-Tublin antibodies.

FIG. 6 shows the results of a study of transcriptional activation of a BAMBI promoter via beta-catenin-TCF. The effects of TCF-4 and ICAT dominant negative mutants on beta-catenin-mediated activation of the BAMBI promoter were studied. COS-1 cells were transfected with a luciferase reporter plasmid (pTOP-tk-luciferase or 575-luc), and luciferase activity was measured.

DETAILED DESCRIPTION OF THE INVENTION

1. Antibody which Recognizes BAMBI Protein

Figure 1:
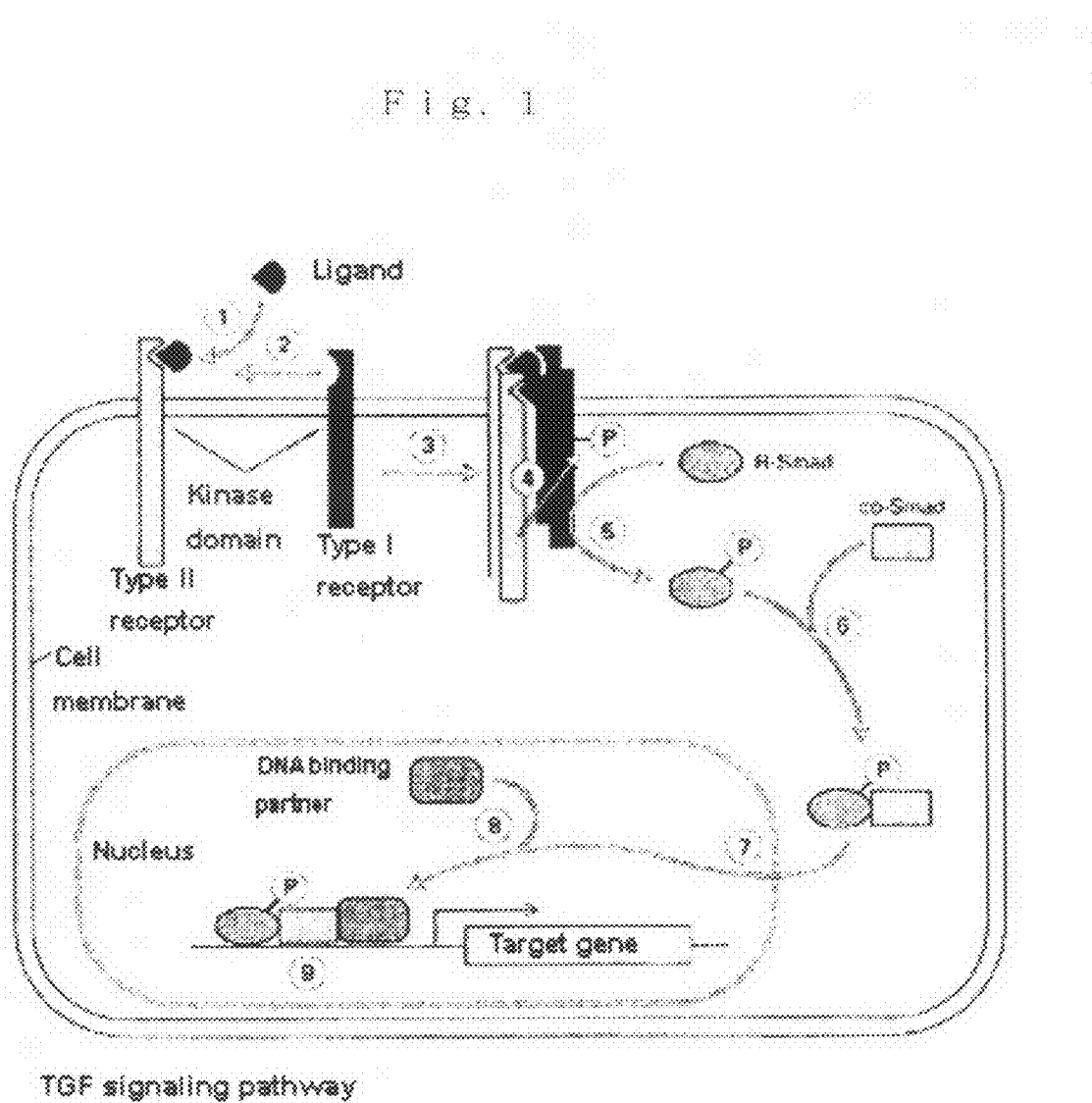
FIG. 1 is an outline of the Wnt signaling system
Figure 3:
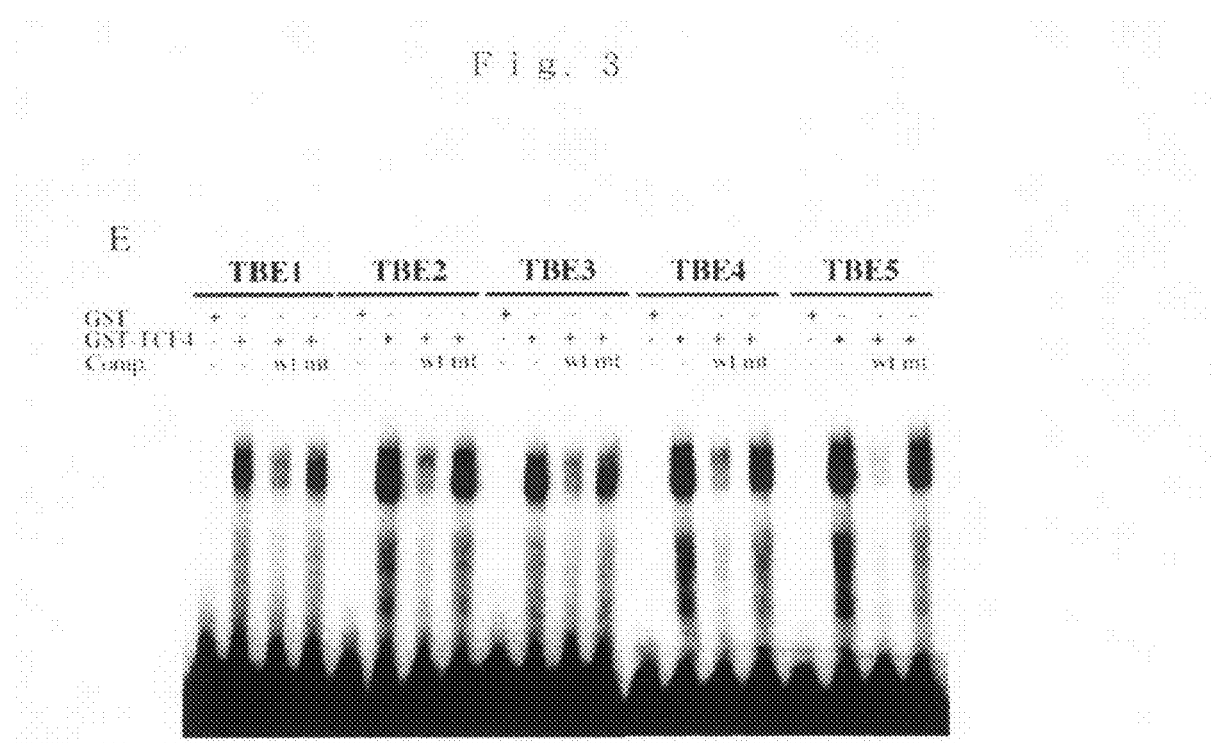
FIG. 3 shows the results of electrophoretic mobility shift assay of the TCF-4DNA binding region. Five TCF-4 binding sequences on intron 1 were synthesized (TBE 1-5) and radioactively labeled, and shift assay was used to investigate whether they bound with GST-TCF. As a result, it was found that TBE 1-5 bind specifically with GST-TCF but do not bind with GST, that binding with GST-TCF4 is no longer detected when a large excess of non-radioactively-labeled TBE 1-5 is present in the reaction liquid, and that TBE 1-5 with introduced mutations do not have such effects.

The "antibody" of the present invention is a whole antibody molecule or fragment thereof that recognizes (or can bind to) the BAMBI protein, which is its antigen, and may be either a polyclonal antibody or a monoclonal antibody. In these specifications, the "BAMBI protein" is a polypeptide having the amino acid sequence of SEQ ID No: 1, a polypeptide having an amino acid sequence containing deletion, substitution or addition of one or more (selected from 1 to 30, 1 to 20, 1 to 10, 1 to 5 or 1 to 2) amino acids as compared to the amino acid sequence of SEQ ID No: 1, or a fragment of these (for example, a fragment comprising 10 to 70 or 20 to 60 or 30 to 50 amino acid residues). The antibody of the present invention encompasses antibody mutants. An "antibody mutant" is a mutant in which one or more (selected from 1 to 30, 1 to 20, 1 to 10, 1 to 5 or 1 to 2) amino acid residues in the antibody have been modified from the original. It is included in the scope of the present invention no matter how the amino acid sequence has been modified as long as it can specifically recognize the BAMBI protein in the same way as the original antibody. Such a mutant has less than 100% sequence homology or similarity with an amino acid sequence having at least 75% or preferably at least 80% or more preferably at least 85% or still more preferably at least 90% or ideally at least 95% amino acid sequence homology or similarity with the amino acid sequence of the variable domain of the heavy chain or light chain of the antibody.

Moreover, the antibody of the present invention may be a human antibody, a humanized antibody, a chimera antibody and an antibody fragment (such as Fab, F(ab')$_2$ and Fv). A "humanized antibody" is a modified antibody from a mouse or other non-human species in which a primary structure other than the complementarity-determining part of the H or L chain has been replaced by a primary structure corresponding to the human antibody. A "chimera antibody" is an antibody having a Fab region or Fc region derived from an antibody of a different species.

In the present invention, "antibody fragment" indicates a part of the whole antibody, generally an antigen-binding region or variable region. For example, antibody fragments include Fab, Fab', F(ab')$_2$ and Fv fragments. Papain digestion of an antibody produces two of the same antigen-binding fragments each having one antigen-binding site, called the Fab fragment, and a remaining fragment called "Fc" because it crystallizes easily. Pepsin digestion produces a F(ab')$_2$ fragment which has two antigen-binding sites and can cross-link with the antigen, and another, residual fragment (called pFc'). Other fragments include diabodies, linear antibodies, single-chain antibody molecules, and polyspecific antibodies formed from antibody fragments.

The "Fv" fragment is the minimum antibody fragment, and includes a complete antigen-recognizing site and binding site. This region is a dimer ($V_H$-$V_L$ dimer) in which the variable domains of one heavy chain and light chain are strongly linked by non-covalent bonding. Three CDRs of each variable domain interact to form an antigen-binding site on the surface of the $V_H$-$V_L$ dimer. The six CDRs contribute an antigen-binding site to the antibody. However, even one variable domain (or half of a Fv comprising only three antigen-specific CDRs) has the ability to recognize and bind to the antigen even though affinity is lower than with the entire antigen-binding site.

The Fab fragment (also called F(ab)) also includes the light chain constant domain and the heavy chain cell constant domain (CH1). The Fab' fragment differs from the Fab fragment in having several additional residues derived from the carboxyl terminus of the heavy chain CH1 domain, including one or more cysteines from the hinge region of the antibody. The antibody of the present invention can be manufactured by any of a variety of methods.

In these specifications, an antibody to the BAMBI protein such as the aforementioned is called an "anti-BAMBI antibody".

The method of preparing the anti-BAMBI antibody is described below.

(1) Preparation of Antigen

Examples of an immunogen to be used in preparing the anti-BAMBI antibody of the present invention include a polypeptide having the amino acid sequence of SEQ ID No: 1 and a polypeptide having an amino acid sequence containing deletion, substitution or addition of multiple amino acids as compared to the polypeptide of SEQ ID No: 1. Of course, other types of BAMBI proteins than the hBAMBI protein having the amino acid sequence of SEQ ID No: 1 can be used as the immunogen. In addition, a fragment comprising an epitope site of hBAMBI can be used. Such a fragment includes, for example, a fragment comprising the region of amino acids 45-147 and the region of amino acids 177-241 of hBAMBI. The immunogen used to manufacture the antibody of the present invention may be a natural BAMBI protein purified from mouse, human or other cells, or a genetically-engineered BAMBI protein or fragment thereof. The immunogen used to manufacture the antibody of the present invention can also be synthesized using a commercial protein synthesizer by specifying its amino acid sequence.

(2) Preparation of Monoclonal Antibodies (i) Collection of Antibody-Producing Cells The protein or peptide prepared as described above is administered as an antigen to mammals such as rats, mice or rabbits. The dose of the antigen per animal is 0.1 to 100 mg without an adjuvant and 1 to 100 μg with an adjuvant. Examples of adjuvants include Freund's complete adjuvant (FCA), Freund's incomplete adjuvant (FIA), aluminum hydroxide adjuvant and the like. Immunization is mainly by intravenous, subcutaneous, intraperitoneal or other injection. There is no particular limit on the interval between immunizations, which can range from several days to several weeks, but 1 to 10 or preferably 2 to 5 immunizations at intervals of 2 to 5 weeks are desirable. Antibody-producing cells are collected 1 to 60 days or preferably 1 to 14 days after the final immunization. The antibody-producing cells may be spleen cells, lymph node cells, peripheral blood cells or the like, but spleen cells or local lymph node cells are preferred.

(ii) Cell Fusion

The antibody-producing cells are fused with myeloma cells to obtain a hybridoma. Commonly available cell lines from mice or other animals can be used as the myeloma cells for fusion with the antibody-producing cells. The cell line used is preferably one that has drug selectivity, and that does not survive in HAT selection medium (comprising hypoxanthine, aminopterin and thymine) in an unfused state but can only survive when fused with antibody-producing cells. Examples of myeloma cells include X63Ag.8.653, NSI/1-Ag4-1, NSO/1 and other mouse myeloma cell lines and YB 2/0 and other rat myeloma cell lines.

Next, The aforementioned myeloma cells and antibody-producing cells are fused. Cell fusion is accomplished by mixing $1 \times 10^6$ to $1 \times 10^7$/ml of antibody-producing cells and $2 \times 10^5$ to $2 \times 10^6$/ml of myeloma cells in DMEM, RPMI-1640 or other animal cell culture medium containing no serum (ratio of antibody-producing cells to myeloma cells preferably 2:1 to 3:1), and performing the fusion reaction in the presence of a cell fusion promoter. Cell fusion promoters that can be used include polyethylene glycol with a mean molecular weight of 1000 to 6000 daltons and the like. The antibody-producing cells and myeloma cells can also be fused using a commercial cell fusion device employing electrical stimulus (such as electroporation).

(iii) Hybridoma Selection and Cloning

The target hybridoma is selected from the cells after cell fusion treatment. One method is to dilute the cell suspension suitably with RPMI-1640 medium containing bovine fetal serum for example, sow about $3 \times 10^5$/well on a microtiter plate, add selection medium to each well and culture while changing the selection medium as necessary. As a result, cells, which develop from about the 14th day after initiation of culture in the selection medium, are selected as the hybridoma.

Next, the culture supernatant of the proliferated hybridoma is screened for the presence of antibodies that react to the BAMBI protein. The hybridoma can be screened by ordinary methods, without any particular limitations. For example, part of the culture supernatant from a well grown as a hybridoma can be collected and screened by enzyme immunoassay, radioactive immunoassay or the like. The fused cells can be cloned by the limiting dilution method or the like. Finally, a hybridoma is established of cells producing monoclonal antibodies that bind specifically to the BAMBI protein.

(iv) Collection of Monoclonal Antibodies

A common cell culture method, ascites formation method or the like can be adopted as the method of collecting the monoclonal antibodies from the established hybridoma. In the cell culture method, the hybridoma is cultured for 7 to 14 days under ordinary culture conditions (such as 37° C., 5% $CO_2$) in an animal cell culture medium such as RPMI-1640 medium containing 10% bovine fetal serum, MEM medium or serum-free medium, and antibodies are obtained from the culture supernatant. In the ascites formation method, about $1 \times 10^7$ cells of the hybridoma are administered intraperitoneally to mammals of the same species from which the myeloma cells were derived to grow large quantities of the hybridoma. 1 to 2 weeks later, the ascites are collected. When purification of the antibodies is necessary in the aforementioned antibody collection method, a known method such as ammonium sulfate fractionation, ion exchange chromatography, gel filtration, affinity chromatography or the like can be selected as appropriate, and purification can be made by a combination of these methods.

(3) Preparation of Polyclonal Antibodies to BAMBI Protein

The antigen purified as described above is administered to mammals such as rats, mice, rabbits or the like. The dose of the antigen per animal is 0.1 to 100 mg without adjuvant or 10 to 1000 μg with adjuvant. Examples of adjuvants include Freund's complete adjuvant (FCA), Freund's incomplete adjuvant (FIA), aluminum hydroxide adjuvant and the like. Immunization is mainly by intravenous, subcutaneous, intraperitoneal or other injection. There is no particular limit on the interval between immunizations, which can range from several days to several weeks, but 1 to 10 or preferably 2 to 5 immunizations at intervals of 2 to 5 weeks is desirable. 6 to 60 days after the final immunization date, antibody titer is measured by ELISA (enzyme-linked immunosorbent assay), EIA (enzyme immunoassay), or RIA (radioimmunoassay), and blood collected on the day with the highest antibody titer is used to obtain anti-serum.

Next, polyclonal antibodies in the anti-serum are applied to an affinity column fixed with BAMBI protein, and antibodies (column adsorbed fraction) which react with the BAMBI protein are collected. The reactivity of the polyclonal antibodies in the anti-serum to the BAMBI protein is measured by ELISA or the like.

Humanized antibodies can be obtained using a common, well-known antibody-production method by immunizing human antibody-producing, transgenic non-human mammals with the immunogen (antigen). Methods of producing humanized antibody-producing non-human mammals and humanized antibody-producing transgenic mice in particular are well known (*Nature Genetics* 7:13-21 (1994); *Nature Genetics* 15:146-156 (1997); Japanese Patent Publication No. H4-504365; Japanese Patent Publication No. H7-509137; International Patent Application No. WO94/25585; *Nature* 368:856-859 (1994); Japanese Patent Publication No. H6-500233, etc.).

2. Therapeutic Agent for Colon Cancer or Liver Cancer

The anti-BAMBI antibody can also be used as an antibody drug. A human chimera antibody or humanized antibody can preferably be used as the antibody which is used as the therapeutic agent of the present invention. The therapeutic agent of the present invention comprises an anti-BAMBI antibody as an effective component, and is effective for the treatment (or prevention) of colon cancer or liver cancer. The dosage, form and method of administering the therapeutic agent of the present invention can be selected appropriately according to the patients (humans or non-human animals). For example, the therapeutic agent of the present invention can be administered orally, parenterally, locally or by another suitable route. Ordinary the dosage of the antibody (which is the active ingredient) is about 1 to 3000 mg per day or preferably 5 mmg to 2000 mg per day, but this can be varied according to the patient's weight and symptoms and the individual administration route. Since the dosage will vary depending on differences in the patient's sensitivity to the drug, the type of drug formulation, the administration period and the interval between administrations, a dosage below the lower limit of the aforementioned range may be appropriate in some cases.

The antibody of the present invention can be administered either alone or together with pharmacologically or pharmaceutically acceptable carriers or diluents, and may be given in one administration or in multiple administrations. More specifically, the therapeutic agent of the present invention can be made into the form of pills, capsules, powder, spray, aqueous suspension, injection, elixir, syrup or the like in combination with various pharmacologically acceptable inactive carriers for example. These carriers include solid diluents or excipients, sterile aqueous media, various non-toxic organic solvents and the like. In general, the therapeutically effective antibody of the present invention is administered at a concentration in the range of 5% to 70% by weight in the aforementioned forms. In the case of oral administration, microcrystalline cellulose, sodium citrate, calcium carbonate, dipotassium phosphate, glycine and various other excipients can be used together with various disintegrators such as starch, alginic acid and some double silicates and with granule-forming binders such as polyvinylpyrrolidone, sucrose, gelatin, and gum arabic. Lubricants such as magnesium stearate, sodium lauryl sulfate, talc and the like are also extremely useful for pill formulation. When oral administration is in the form of an aqueous suspension and/or elixir, an emulsifier and/or suspending agent may be included as necessary, together with a diluent such as water, ethanol, propylene glycol, glycerin or the like and combinations of these. In the case of parenteral administration, the active ingredient of the present invention can be dissolved in either sesame oil or peanut oil, or else dissolved in an aqueous solution of propylene glycol and used in solution. The aqueous solution can be buffered appropriately as necessarily (preferably to pH 8 or more), and the liquid diluent needs to be first made isotonic. Such an aqueous solution is suited to intravenous injection, while the oily solution is suited to intra-articular injection, intramuscular injection and subcutaneous injection.

3. Diagnostic Agent Containing Anti-BAMBI Antibody of the Present Invention

Because the anti-BAMBI antibody of the present invention, particularly the monoclonal antibody can detect and assay the BAMBI protein, it can be used for diagnosing colon cancer or liver cancer. The method of diagnosing colon cancer or liver cancer using this antibody includes for example (a) a step of reacting the monoclonal antibody of the present invention or a fragment thereof with a sample, and (b) a step of reacting the antigen-antibody complex formed in (1) with a labeled antibody for purposes of detection. The diagnostic method using the diagnostic agent of the present invention may be any method as long as it is a method of assay using antibodies or in other words an immunoassay, and examples include enzyme-linked immunoassay (ELISA), fluorescence immunoassay, radioimmunoassay (RIA), luminescence immunoassay, immunoenzymatic technique, fluorescent antibody technique, turbidimetric immunoassay, latex agglutination assay, latex turbidimetric assay, hemagglutination, particle agglutination or Western blotting.

There are no particular limits on the sample used in the detection and/or assay of the present invention, which may be any biological sample that might contain BAMBI protein, such as blood, serum, plasma, lymphocyte culture supernatant, urine, cerebrospinal fluid, saliva, sweat, ascites or amniotic fluid or a cell or organ extract or the like. When the detection and/or assay method of the present method is an immunoassay method using labeled antibodies such as enzyme-linked immunoassay, fluorescence immunoassay, radioimmunoassay, luminescence immunoassay or the like, the sandwich method or competitive method can be applied, and in the case of the sandwich method either or both of the solid phase antibody and the labeled antibody is the monoclonal antibody of the present invention.

A labeled antibody is an antibody labeled with a labeling substance, and such labeled antibodies can be used for detecting or assaying antigen (that is, Ebola virus nuclear proteins) contained in a sample (for example, blood or other body fluid, culture supernatant, centrifuged supernatant or the like). There are no particular limits on what labeling substance can be used in the present invention as long as it can bind to antibodies by means of physical binding, chemical binding or the like, thus allowing them to be detected. Specific examples of labeling substances include enzymes, fluorescent substances, chemiluminescent substances, biotin, avidin, radioactive isotopes and the like, and more specific examples include peroxidase, alkaline phosphatase, beta-D-galactosidase, glucose oxidase, glucose-6-phosphate dehydrogenase, alcohol dehydrogenase, malic acid dehydrogenase, penicillinase, catalase, apo-glucose oxidase, urease, luciferase, acetylcholine esterase and other enzymes, fluorescein isothiocyanate, phycobiliproteins, rare earth metal chelates, dansyl chloride, tetramethylrhodamine isothiocyanate and other fluorescent substances, $^3$H, $^{14}$C, $^{125}$I, $^{131}$I and other radioactive isotopes, and biotin, avidin and other chemiluminescent substances. A known method such as the glutaraldehyde method, maleimide method, pyridyl disulfide method, periodic acid method or the like can be used to bind the labeling substance to the antibody.

The radioactive isotopes and fluorescent substances here independently produce detectable signals, but the enzymes, chemiluminescent substances, biotin and avidin do not independently produce detectable signals, but instead product detectable signals when they react with at least one other substance. For example, in the case of an enzyme at least a substrate is required, and a variety of substrates are used depending on the method of measuring enzyme activity (colorimetry, fluorescence method, bioluminescence method or chemoluminescence method). In the case of biotin generally at least avidin or enzyme-modified avidin is reacted. A variety of colorants dependent on the substrate can also be used as necessary.

The fixed antibody can be used to detect, assay, isolate or purify an antigen contained in a sample (such as plasma or other bodily fluid, culture supernatant, centrifuged supernatant or the like). Examples of insoluble carriers which can be used to fix the antibody include (1) plates, containers with content volume such as test tubes, and beads, balls, filters, membranes and the like made of materials which are insoluble in water such as glass and plastics made of polystyrene resin, polycarbonate resin, silicon resin, nylon resin or the like, and 2) insoluble carriers used in affinity chromatography, such as cellulose carriers, agarose carriers, polyacrylamide carriers, dextran carriers, polystyrene carriers, polyvinyl alcohol carriers, polyamic acid carriers, porous silica carriers and the like.

4. Colon Cancer or Liver Cancer Detection Kit Using Anti-BAMBI Antibody of the Present Invention The detection kit of the present invention comprises the anti-BAMBI antibody of the present invention, preferably the monoclonal antibody. The antibody used here may be the aforementioned fixed antibody or labeled antibody. For example, when the antibody of the present invention is used as a primary antibody, the kit of the present invention may contain a secondary antibody for detecting a complex formed from an antigen-antibody binding reaction. The kit of the present invention may also contain various auxiliary substances other than antibodies to enable the kit to be used easily and efficiently. Examples of auxiliary substances include solvents for dissolving a secondary antibody in solid form, cleansers to be used for cleaning undissolved carrier, substrates for measuring enzyme activity when an enzyme is used as the antibody labeling substance, and substances such as reaction arresters that are commonly used in immunoassay reagent kits.

The present invention also encompasses a diagnostic agent and method for diagnosing colon cancer or liver cancer by detecting BAMBI mRNA by means of a nucleic acid amplification method such as PCR, RT-PCR or the like using a primer designed based on a gene encoding BAMBI, and a diagnostic agent and diagnostic method comprising a probe designed based on a fragment of a gene encoding BAMBI.

A primer consisting of 15 or more or preferably between 20 and 50 contiguous nucleotides of the nucleotide sequence according to SEQ ID No: 2 can be used as the primer in the present invention. A primer set can be designed so that the distance between the forward primer and reverse primer is preferably 500 nucleotides or less. The primers can also comprise as necessary sequence parts not complementary to the target BAMBI gene, and tag sequences can also be added for example.

A BAMBI gene fragment comprising a sequence characteristic of BAMBI, preferably with a nucleotide length of 50 to 150 bp, is used as the probe in the present invention. The probe can be labeled for example with the radioactive label $^{32}$P. The probe can also be fluorescence labeled, luminescence labeled, enzyme labeled or the like as necessary. A person with skill in the art can detect the BAMBI gene by a detection method suited to the labeling substance used. A biotinylated probe can also be used, and a method of treating of treating this probe with fluorescent avidin dye and detecting the fluorescence is possible.

5. Therapeutic Agent for Colon Cancer or Liver Cancer Containing Double-Stranded RNA Moreover, the present invention encompasses a therapeutic agent for colon cancer or liver cancer which specifically breaks down BAMBI mRNA by means of RNA interference (RNAi). Double-stranded RNA 21 to 25 nucleotides in length which generates RNA interference, such as dsRNA (double strand RNA), siRNA (small interfering RNA) or shRNA (short hairpin RNA), is used by preference, and can be locally transported to a desired site by means of liposome or another transportation system, or can be caused to be locally expressed using a vector in which the aforementioned double-stranded RNA is produced. Such double-stranded RNA can be used as a research tool for suppressing expression of BAMBI. Methods of preparing and using such double-stranded RNA (dsRNA, siRNA or shRNA) are widely reported (see Patent Publication 2002-516062; U.S. Patent Publication 2002/086356A; Nature Genetics 24(2), February, 180-183; Genesis 26(4), April, 240-244; Nature, Spe. 21, 407:6802, 319-20; Genes & Dev., Vol. 16 (8), April 16, 948-958; Proc Natl. Acad. Sci. USA 99(8), 16 April, 5515-5520; Science 296 (5567), 19 April, 550-553; Proc. Natl. Acad. Sci. USA April 30, 99:9, 6047-6052; Nature Biotechnology, Vol. 20(5), May, 497-500; Nature Biotechnology Vol. 20(5), May, 500-508; Nucleic Acids Res., May 15, 30:10, e46).

Moreover, the anti-BAMBI antibody of the present invention can be used as a system for drug transport into colon cancer and liver cancer cells. For example, an anti-BAMBI antibody-drug inclusion complex can be used which consists of the anti-BAMBI antibody bound to a drug inclusion. Examples of drugs include anti-cancer low-molecular-weight drugs and high-molecular-weight toxins, MTX, adriamycin, diphtheria toxin, lysine and the like.

EXAMPLES

The present invention is explained in more detail below based on examples.

Reference Example 1

Preparation of hBAMBI, Beta-Catenin-Expressing Adenovirus Vector, hBAMBI-Expressing Vector (1) Construction of Plasmid and Recombinant Virus To construct an hBAMBI-luciferase reporter plasmid, human BAC clone RPCI-13-43N24 comprising the entire lengths of the promoter region, exon and intron was purchased from BACPAC resources. The longest, 7.3 kb construct or a deletion mutant construct thereof was prepared by cloning the respective DNA fragments into suitable restriction enzyme cleavage sites of the pGL3-promoter vector (Promega).

A point mutation in the TCF/LEF binding sequence was produced by standard PCR using Pyrobest DNA polymerase (Takara). The following primers were used. (The substituted nucleotides are underlined):

```
TBE1:
5'-GCTGCAGAGGATTGATTAGCGGTAG-3'        (SEQ ID No: 6)
and

5'-CTACCGCTAATCAATCCTCTGCAGC-3';       (SEQ ID No: 7)

TBE2:
5'-CTCTGTGTCTAGTTAAATGTATCTCTG-3'      (SEQ ID No: 8)
and

5'-CAGAGATACATTTAACTAGACACAGAG-3';     (SEQ ID No: 9)

TBE3:
5'-CTCTAAGTGTAGTTATATCTCTGAATG-3'      (SEQ ID No: 10)
and

5'-CATTCAGAGATATAACTACACTTAGAG-3';     (SEQ ID No: 11)

TBE4:
5'-CTGGAAATATAGAAAGCGGGCAGAAC-3'       (SEQ ID No: 12)
```

-continued and

5'-GTTCTGCCCGC<u>T</u>TTC<u>T</u>ATATTTCCAG-3'; (SEQ ID No: 13)

TBE5:
5'-CTAAAAGTTCATGC<u>A</u>GTT<u>A</u>AATTTGGG-3' (SEQ ID No: 14)

and

5'-CCCAAATT<u>T</u>AA<u>C</u>TGCATGAACTTTTAG-3'. (SEQ ID No: 15)

pTOP-tk-luciferase and pFOP-tk-luciferase were provided by V. Korinek and H. Clevers (University Medical Center, Utrecht, The Netherlands). An adenovirus having introduced Icat and LacZ with added myc tags was prepared by methods already described (Sekiya et al. *Cancer Res.* 62, 3322-3326 (2002)). An adenovirus vector expressing stable beta-catenin with tyrosine substituted for serine in the 33rd position was prepared by using a pAdenoXTM expression system (Clontech) in accordance with the attached manual. The GFP-fused full-length hBAMBI-expressing vector pEGFP-N3-hBAMBI was prepared by cloning an RT-PCR product to the pEGFP-N3 vector (Clontech). Specifically, total RNA extracted from human colon cancer cells SW48 was subjected to reverse transcription, and amplified by PCR using the primers 5'-CATGAATTCCGCCACCATGGATCGC-CACTCCAGCTAC-3' (SEQ ID No: 16) and 5'-CATCTC-GAGTACGAACACCAGCAACCCGTGC-3' (SEQ ID No: 17) for amplifying the full-length hBAMBI ORF, to obtain full-length hBAMBI. Since this amplification product has an EcoRI cleavage site and XhoI cleavage site added to both ends, these can be treated with restriction enzymes and inserted into the EcoRI and SalI sites of the pEGFP-N3 vector (Clontech) multi-cloning sites to construct pEGFP-N3-hBAMBI. This pEGFP-N3-hBAMBI construct has the hBAMBI gene and GFP gene connected in frame, and when expressed in mammalian cells, it expresses a full-length hBAMBI protein with the GFP protein added to the carboxyl terminus.

A GFP-expressing vector was also constructed in the same way for a deletion mutant of hBAMBI (hBAMBIDN) lacking amino acids #20-131.

Reference Example 2

Preparation of GST-TCF4 Fused Protein

Electrophoretic Mobility Shift Assay (EMSA)

A GST-TCF4 fused protein was prepared using the following primers and the PCR product of a sequence encoding amino acids #265-496 of human TCF4:

(SEQ ID No: 18)
5'-CATGAATTCGCTTCCGTGTCCAGGTTCCCTCC-3' and (SEQ ID No: 19)
5'-CATCTCGAGCTAGCCTAGCAGGTTCGGGGAGGG-3'.

The PCR product was cloned into pGEX-5X-1 (Pharmacia). GST and GST-TCF4 were purified from the *E. coli* DH-5α strain. The DNA binding assay was performed by published methods (Tago et al., *Gene & Development* Vol. 14, p. 1741-1749).

The probes were annealed together in the following combinations:

5'-GCTGCAGAGGCTTTGTTAGCGGTAG-3' (SEQ ID No: 20)

and

5'-CTACCGCTAACAAAGCCTCTGCAGC-3', (SEQ ID No: 21)

5'-CTCTGTGTCTCTTTGAATGTATCTCTG-3' (SEQ ID No: 22)

and

5'-CAGAGATACATTCAAAGAGACACAGAG-3', (SEQ ID No: 23)

5'-CTCTAAGTGTCTTTGTATCTCTGAATG-3' (SEQ ID No: 24)

and

5'-CATTCAGAGATACAAAGACACTTAGAG-3', (SEQ ID No: 25)

5'-CTGGAAATATCAAAGGCGGGCAGAAC-3' (SEQ ID No: 26)

and

5'-GTTCTGCCCGCCTTTGATATTTCCAG-3', (SEQ ID No: 27)

5'-CTAAAAGTTCATGCCTTTGAATTTGGG-3' (SEQ ID No: 28)

and

5'-CCCAAATTCAAAGGCATGAACTTTTAG-3'. (SEQ ID No: 29)

The oligonucleotide used in preparing the mutant hBAMBI-luciferase construct was used as the mutant competitive molecule.

Reference Example 3

Preparation of Cells and Pathological Samples

All cells were cultured in a single layer using appropriate medium. COS-1, DU-145, HepG2 and Alexander cells were cultured in DMEM medium (Nissui), SW48 and SW480 cells in Leibovit's L-15 medium (Sigma) and HCT116 cells in McCoy's SA medium (Sigma) with 10% bovine fetal serum (JCS) added to each. All cells were cultured under moisturizing conditions of 5% $CO_2$ in an incubator set to 37° C. The cancer tissues and control non-cancer tissues were surgically removed with the informed consent of the patients.

Reference Example 4

ICAT and DN-TCF4 were made to be expressed in colon cancer strain SW48 using an adenovirus vector, and changes in mRNA or the expressed amount of the protein were measured by semi-quantitative RT-PCR or immunoblotting.

In addition, beta-catenin S33Y is an active mutant beta-catenin with the serine residue replaced by a tyrosine residue in the $33^{rd}$ position. This mutant has been found in colon cancer cells. This was made to be expressed in 293 cells using an adenovirus, and the expressed amount of BAMBI was measured.

(1) Semi-Quantitative RT-PCR

Figure 4:
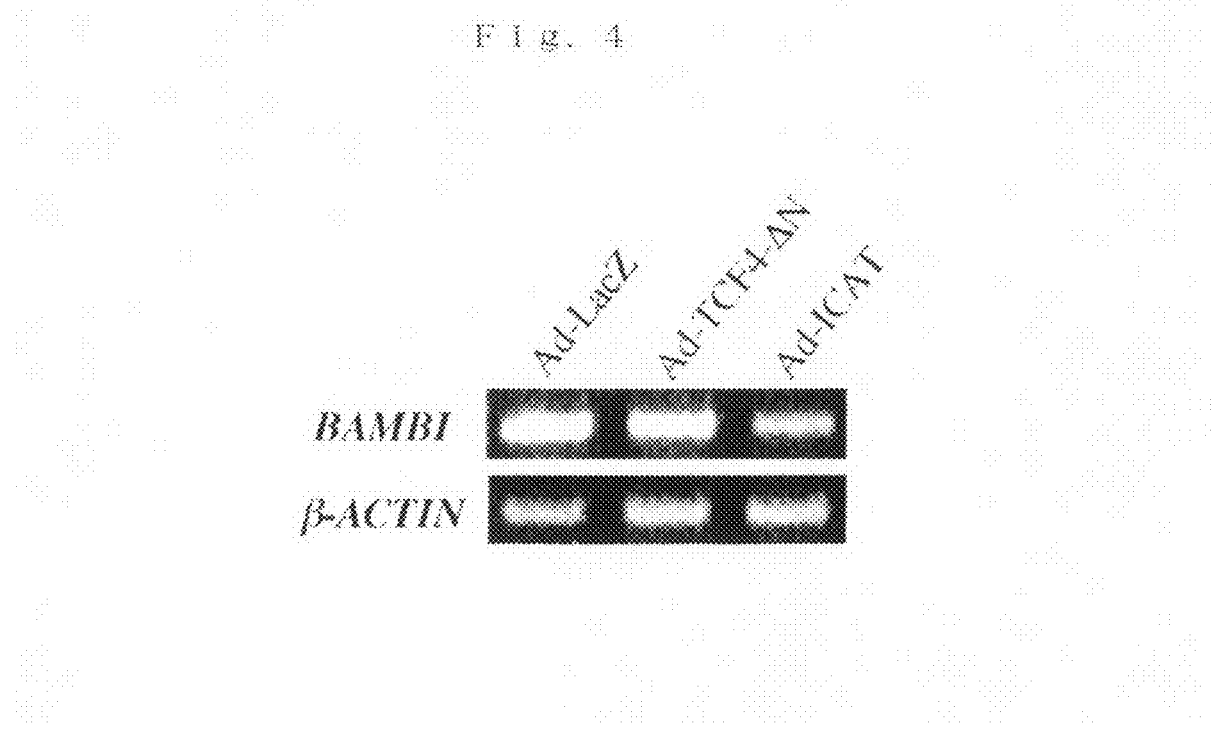
FIG. 4 shows the results when ICAT and TCF-4 dominant negative mutants were expressed using adenovirus vectors in colon cancer cell line SW48, and RNA was extracted and subjected to semi-quantitative RT-PCR analysis using primers specific for BAMBI and beta-actin. BAMBI expression was suppressed by means of transcriptional activation via beta-catenin-TCF.

Total RNA was extracted using NucleoSpin (Macherey-Nagel). The total RNA (20 μg per lane) was electrophoresed using formaldehyde-containing 1% agarose gel, and transcripted to Hybond-N$^+$ (Amersham Pharmacia Biotech). A $^{32}$P-labeled cDNA probe unique to the target gene was hybridized, and detected with AS1500 (Fuji Film). The results are shown in FIG. 4.

(2) Immunoblotting

Immunoblotting was performed by the methods described above (Matsumine et al., 1996). It was found that (1) ICAT suppresses BAMBI expression, (2) the dominant negative TCF4 mutant (DN-TCF4) also suppresses BAMBI expression and (3) BAMBI expression is promoted by the action of the active mutant beta-catenin. The results are shown in FIG. 5.

Reference Example 5

<Analysis of BAMBI Promoter>

Reporter constructs were prepared with the BAMBI promoter linked to luciferase, and promoter activity was measured by luciferase assay.

(1) Luciferase Reporter Assay

The effects of TCF-4 and ICAT dominant negative mutant on activation of the BAMBI promoter by means of beta-catenin were studied by transfecting luciferase reporter plasmids (pTOP-tk-luciferase or -575-luc) into COS-1 cells and measuring luciferase activity.

The cells were seeded on 12-well dishes 18 hours before transfection. Transfection was performed using Lipofectamine PLUS (Invitrogen) in accordance with the attached protocols. The luciferase assays were performed using a Dual-Luciferase Reporter Assay System (Promega) in accordance with the attached protocols.

As a result, it was found that (1) the BAMBI promoter is activated by beta-catenin S33Y and inactivated by DC-TCF4 and ICAT. The results are shown in FIG. 6.

Example 1

Detection of Colon Cancer with Anti-BAMBI Antibodies (1) Preparation of Anti-BAMBI Antibodies Antibodies to the N and C termini were prepared by affinity purification using as the antigen serum from rabbits (New Zealand White) which had been immunized with GST-fused proteins comprising the region of amino acids #45-147 and the region of amino acids #177-241 of hBAMBI, respectively, which were made to be expressed in *E. coli*. Mouse monoclonal antibodies to beta-catenin were purchased from Transduction Laboratories. Mouse monoclonal antibodies to alpha-tubulin were purchased from Oncogene TM.

(2) Immunohistochemical Analysis Using Anti-BAMBI Antibodies

Paraffin-embedded tissue sections were immune stained by standard methods. Generally speaking, the paraffin was removed with xylene, and the sections were then hydrated with special grade ethanol/distilled water. The slides were placed in a citric acid buffer (pH 6.0), ultrasound treated for 15 minutes, and then incubated overnight at 4° C. with labeled antigen. The stain patterns were made visible with RITC-labeled anti-mouse antibodies and FITC-labeled anti-rabbit antibodies, respectively. The sections were observed and photographed under a confocal microscope.

Figure 7:
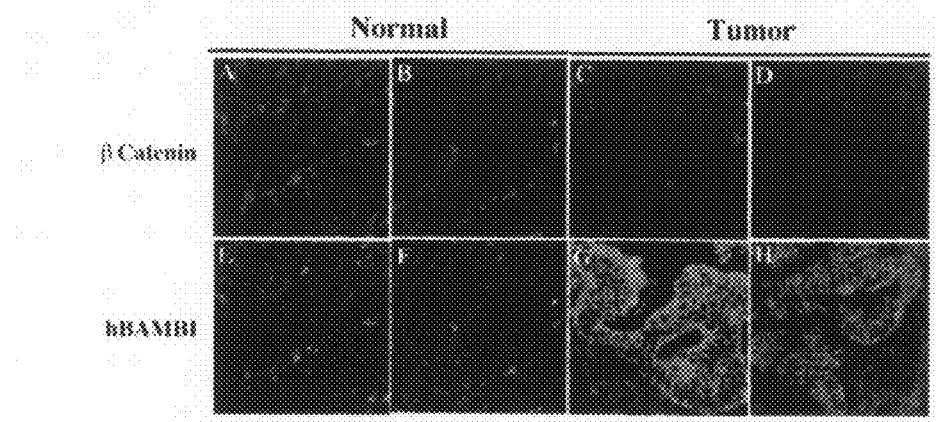
FIG. 7 shows the results of double staining of human colon cancer tissue and neighboring non-cancer tissue using anti-beta-catenin antibodies and anti-BAMBI N-terminal antibodies and C-terminal antibodies to investigate expression of BAMBI in colon cancer.

As a result, BAMBI expression was found to be high in colon cancer and low in normal parts. The results are shown in FIG. 7.

Example 2

(1) Semi-Quantitative RT-PCR

BAMBI expression was investigated by RT-PCR in 18 cases of colon cancer and 10 cases of liver cancer. Total RNA was extracted from cancer tissue and control non-cancer tissue using NucleoSpin (Macherey-Nagel). First chain cDNA was synthesized using a random hexamer and Superscript II reverse transcriptase (Invitrogen). 1 μl cDNA of each kind of sample was used in the respective PCR reactions using a PTC-2000 Peltier Thermal Cycler (MJ Research). The primers used in PCR were as follows:

```
hBAMBI primers:
5'-CAGGGGTGAGGCCTCAGGAC-3'      (SEQ ID No: 30)

and

5'-CAAATTCCAGCTCCCTTGGATGC-3';  (SEQ ID No: 31)

Axin 2:
5'-GCCAGCCGGCACCATCTGTG-3'      (SEQ ID No: 32)

and

5'-CGAAGCCCACTGGCCGATTC-3';     (SEQ ID No: 33)

Beta-actin:
5'-ACACTGTGCCCATCTACGAG-3'      (SEQ ID No: 34)

and

5'-AGTCGTGCTTGCTGATCCAC-3'.     (SEQ ID No: 35)
```

The PCR conditions were 3 minutes of initial heat denaturing at 94° C. followed by 30 cycles (for hBAMBI), 32 cycles (for Axin2), or 23 cycles (for β-ACTIN) of 30 seconds at 94° C., 30 seconds at 62° C., and 30 seconds 72° C. All PCR reactions were performed with 25 μl of reaction and with 3 minutes of initial heat denaturing at 94° C. followed by an amplification reaction in cycles of 30 seconds at 94° C., 30 seconds at 62° C., and 1 minute at 72° C. The PCR product was electrophoresed on 1% agarose gel and detected by staining with ethidium bromide.

Figure 8:
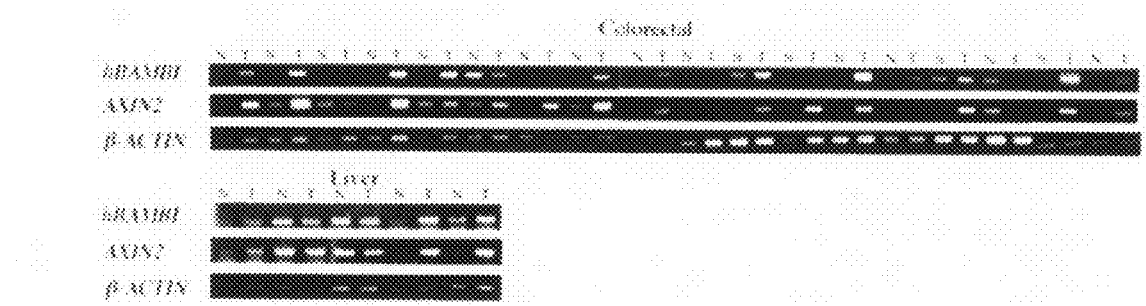
FIG. 8 shows expression of BAMBI in colon cancer tissue and liver cancer tissue according to semi-quantitative RT-PCR. Expressed amounts of BAMBI and AXIN were investigated by semi-quantitative RT-PCR(N=non-cancer tissue, T=cancer tissue).

As a result, elevated expression of BAMBI was seen in 13 out of 18 cases of colon cancer and 3 out of 10 cases of liver cancer. The results are shown in FIG. 8.

Example 3

BAMBI was made to be expressed in prostate cancer Du145 (which has low BAMBI expression), and subjected to focus assay with or without the presence of TGF-beta. The resulting focus was picked up and cultured, and the strength of induction of transcriptional activation by TGF-beta was measured by luciferase assay.

A colony-forming assay was performed as follows. The Du145 cells were transfected with the target plasmid 1 day before seeding using Lipofectamine 2000 (Invitrogen) in accordance with the attached protocols. The cells ($5 \times 10^5$ cells) were seeded on 10 cm dishes, selected with 400 mg/ml G418 (Gibco), and cultured with or without addition of 1 ng/ml TGF-beta 1. Medium exchange and TGF-beta 1 stimulus were performed at 5-day intervals. 3 weeks after seeding, the colonies were either stained with methylene blue or isolated for further testing.

Figure 9:
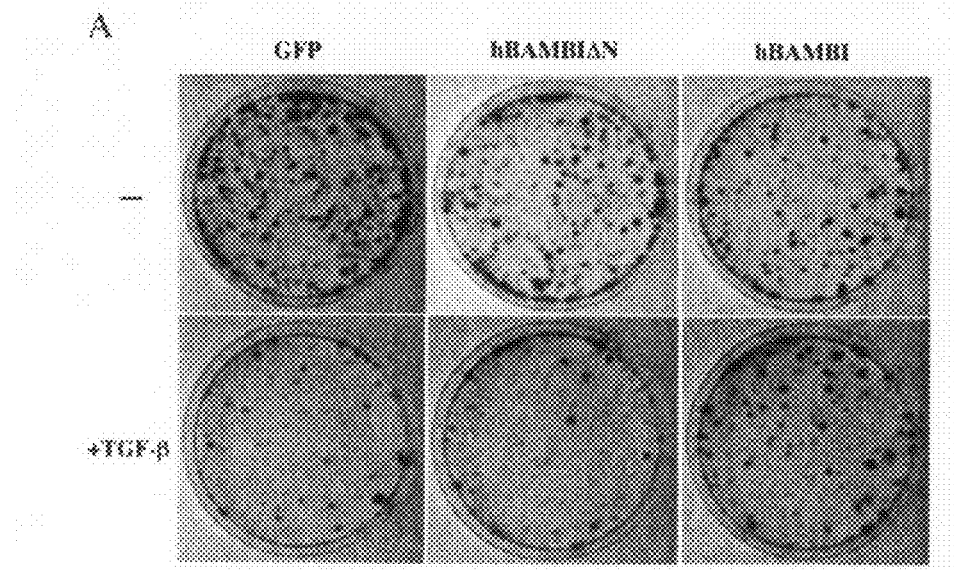
FIG. 9 shows that BAMBI blocks the growth-inhibiting effects of TGF-beta. These results are from a colony formation assay in which the plasmid shown in the figure was transfected into DC-145 cells, which were then cultured for 3 weeks in medium containing 400 μg/ml of geneticin with or without TGF-beta.

As a result it was found that while TGF-beta strongly inhibits the growth of Du145 cells, this inhibition by TGF-beta is blocked when BAMBI is expressed, and that Du-145 cells that express BAMBI have high sensitivity to the TGF-beta signal, resulting in stronger transcriptional activation of the target gene. The results are shown in FIG. 9.

Example 4

BAMBI RNAi was made to be expressed in colon cancer Alexander cells and liver cancer HepG2 cells, which had high BAMBI expression, and a luciferase assay was performed.

DNA oligonucleotides encoding the following siRNA were subcloned to pSUPER (Brummelkamp et al) and used:

```
siRNA-1:    CCACTCTGGCACCACCATA   (SEQ ID No: 3)
siRNA-4:    CAGATGCTCTCCCGTTTGC   (SEQ ID No: 4)
siRNA-9:    CTGCTGTCTGACCTGTGAT.  (SEQ ID No: 5)
```

Figure 10:
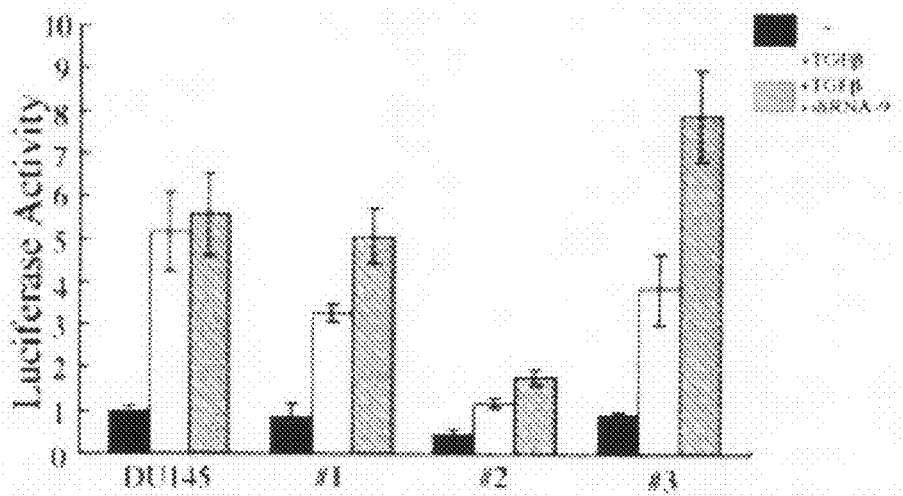
FIG. 10 shows activation of transcription by BAMBI via TGF-beta. Using a p3TP-lux reporter comprising the TGF-beta response sequence of the PAI-1 promoter upstream from the luciferase reporter gene, the effects of BAMBI-GFP on transcription activation mediated by TGF-beta were investigated in DU145 cells.

The results are shown in FIG. 10.

As a result, BAMBI expression was reduced by shRNA RNAi. It appeared that when BAMBI expression was reduced the cancer cells became more sensitive to the TGF-beta signal, enhancing transcriptional activation of the target gene.

Example 5

Lysate was collected from 293T cells transfected with pEGFP-C2 (GFP) and pEGFP-N3-hBAMBI (BAMBI-GFP), and subjected to Western blotting. A uniform 30 μg of protein was loaded into each lane.

Anti-BAMBI amino-terminal rabbit polyclonal antibodies (200× dilution) and anti-BAMBI mouse monoclonal antibodies 6G (10× dilution, 100× dilution) were used as the antibodies. The anti-BAMBI amino-terminal rabbit polyclonal antibodies and anti-BAMBI mouse monoclonal antibodies 6G were prepared as follows.

(Preparation of Anti-BAMBI Amino-Terminal Rabbit Polyclonal Antibodies)

500 mg each of GST-fused hBAMBI aa 45-147 for preparing the anti-BAMBI N-terminal antibodies and 500 mg of aa177-241 for preparing the anti-BAMBI C-terminal antibodies were each mixed with Adjuvant Complete Freund (Difco), and injected subcutaneously into 2 New Zealand White rabbits each for the initial immunization. Next, 200 mg of GST-fused hBAMBI aa 45-147 for preparing the anti-BAMBI N-terminal antibodies and 200 mg of aa 177-241 for preparing the anti-BAMBI C-terminal antibodies were each mixed with Adjuvant Complete Freund (Difco), and injected subcutaneously into rabbits at 2 week intervals for the subsequent immunizations. Following about 5 subsequent immunizations, about 50 ml of blood was collected from the rabbits' ear arteries, incubated for 2 hours at 37° C., and then incubated overnight at 4° C. The next day, following centrifugation for 10 minutes at 3000 rpm, 4° C., the supernatant was poured off and used as the anti-BAMBI antiserum. The antiserum was first passed through a column filled with particles consisting of GST bound to beads to remove the antibodies that bound to the GST. Next it was passed through a column filled with particles consisting of antigen bound to beads so that antibodies that bound specifically to the antigen were adsorbed by the column. The adsorbed antibodies were then eluted and used as the anti-BAMBI polyclonal antibodies.

(Preparation of Anti-BAMBI Mouse Monoclonal 6G)

3 BALB/C mice were immunized twice subcutaneously on the back with GST-fused hBAMBI aa 45-147, first with 200 μg and then with 50 μg after 2 weeks. The antigen was mixed at a 1:1 ratio with Freund's complete adjuvant (FCA) in the first case and with Freund's incomplete adjuvant (FIA) subsequently for purposes of immunization. Serum was obtained from blood collected from the caudal vein, and the individual with the highest serum titer was sacrificed and spleen cells collected 25 days after the final immunization. The spleen cells were mixed 5:1 with myeloma cells using P3U1 (P3X63 Ag8U.1), and cell fused using polyethylene glycol solution Hybri-Max, 50% w/v (Sigma). $2 \times 10^5$ spleen cells/well were seeded on a microtiter plate and an antibody-producing hybridoma was obtained using HAT Media Supplement (50×) Hybri-Max (Sigma). For the screening, part of the culture supernatant was collected 11 days after fusion and subjected to ELISA using an EIA plate with GST or GST-fused hBAMBI aa 45-147 in the solid phase, and those wells that reacted only with the GST-fused hBAMBI aa 45-147 were selected. These were cloned a total of three times by the limiting dilution method. Finally, a hybridoma was established of cells producing monoclonal antibodies that bound specifically to the BAMBI protein. The hybridoma was cultured for 26 days in RPMI-1640 medium containing 10% bovine fetal serum, and anti-BAMBI monoclonal antibodies were collected from the culture supernatant.

Figure 11:
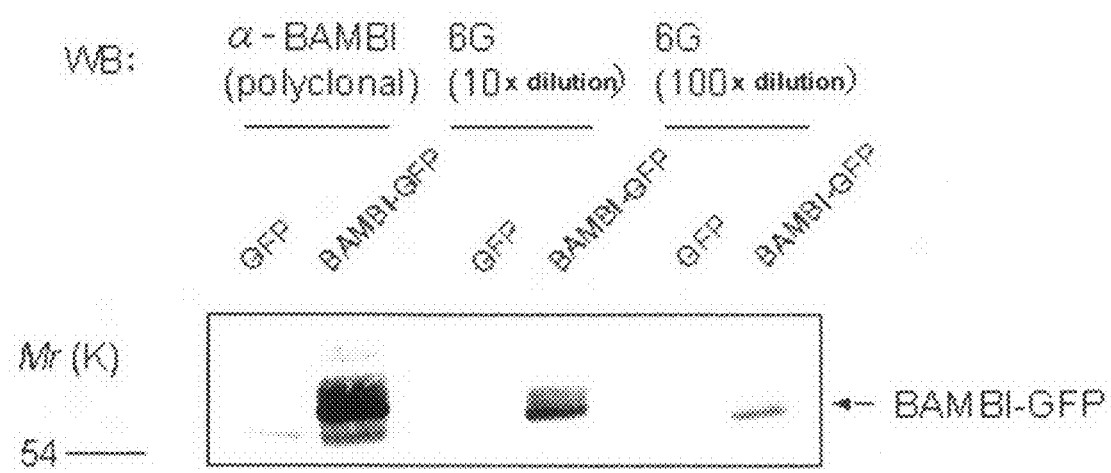
FIG. 11 shows the results of Western blotting to show that anti-BAMBI amino terminal rapid polyclonal antibodies (diluted 200 times) and anti-BAMBI mouse monoclonal antibodies 6G (diluted 10 and 100 times) recognize the BAMBI protein.

The results of Western blotting are shown in FIG. 11. As shown in FIG. 11, anti-BAMBI mouse monoclonal antibody 6G specifically recognizes the BAMBI protein.

The anti-BAMBI antibody of the present invention can be used as the effective component of a therapeutic agent for colon cancer or liver cancer. Moreover, the present invention is excellent for practical use, allowing the detection of colon cancer or liver cancer, which were difficult to detect in the past, through the use of an anti-BAMBI antibody, BAMBI detection primer or BAMBI detection probe. Also, since the present invention can recognize whether a colon cancer is of the type that expresses BAMBI it can be used as an indicator for whether or not therapy that suppresses BAMBI will be effective.

The present invention allows treatment of colon cancer or liver cancer, which was difficult in the past, through the use of anti-BAMBI antibodies or RNA interference using double-stranded RNA based on the BAMBI gene. In particularly, it is expected that the therapeutic agent of the present invention will improve the growth-inhibiting effect of TGF-beta when this effect has been reduced by BAMBI.

What is claimed is:

1. A diagnostic agent for diagnosing colon cancer or liver cancer, comprising a monoclonal antibody or monoclonal antibody fragment wherein said antibody or antibody fragment binds to a polypeptide consisting of the amino acid sequence of SEQ ID No: 1 in the region of amino acids 45 through 147, or amino acids 177 through 241.

2. A therapeutic agent for treating colon cancer or liver cancer, comprising a monoclonal antibody or monoclonal antibody fragment wherein said antibody or antibody fragment binds to a polypeptide consisting of the amino acid sequence of SEQ ID No: 1 in the region of amino acids 45 through 147, or amino acids 177 through 241.

3. The diagnostic agent of claim 1, wherein said antibody fragment is a Fab fragment, a Fab' fragment, a F(ab')$_2$ fragment, or a Fv fragment.

4. The diagnostic agent of claim 1, wherein said antibody is a human chimera antibody or a humanized antibody, or said antibody fragment is a fragment of a human chimera antibody or a humanized antibody.

5. The therapeutic agent of claim 2, wherein said antibody fragment is a Fab fragment, a Fab' fragment, a F(ab')$_2$ fragment, or a Fv fragment.

6. The therapeutic agent of claim 2, wherein said antibody is a human chimera antibody or a humanized antibody, or said antibody fragment is a fragment of a human chimera antibody or a humanized antibody.

7. The diagnostic agent of any one of claims 1, 3 or 4, wherein said antibody or antibody fragment is labeled with peroxidase, alkaline phosphatase, beta-D-galactosidase, glucose oxidase, glucose-6-phosphate dehydrogenase, alcohol dehydrogenase, malic acid dehydrogenase, penicillinase, catalase, apo-glucose oxidase, urease, luciferase, acetylcholine esterase, fluorescein isothiocyanate, phycobiliprotein, rare earth metal chelate, dansyl chloride, tetramethylrhodamine isothiocyanate, chemiluminescent substances, $^3$H, $^{14}$C, $^{125}$I, $^{131}$I, biotin, or avidin.

8. A monoclonal antibody or a monoclonal antibody fragment which binds to a polypeptide consisting of the amino acid sequence of SEQ ID NO: 1 in the region of amino acids 45 through 147.

9. A monoclonal antibody or a monoclonal antibody fragment which binds to a polypeptide consisting of the amino acid sequence of SEQ ID NO: 1 in the region of amino acids 177 through 241.

10. The monoclonal antibody fragment of claim 8 or 9, wherein said antibody fragment is a Fab fragment, a Fab' fragment, a F(ab')$_2$ fragment, or a Fv fragment.

11. The monoclonal antibody or monoclonal antibody fragment of claim 8 or 9, wherein said antibody is a human chimera antibody or a humanized antibody, or said antibody fragment is a fragment of a human chimera antibody or a humanized antibody.

* * * * *